United States Patent [19]

Yamashita et al.

[11] 4,269,485
[45] May 26, 1981

[54] METHOD FOR FOCUSING AN OBJECTIVE LENS OF ENDOSCOPE

[75] Inventors: Nobuo Yamashita, Tama; Miwako Maeda, Hino, both of Japan

[73] Assignee: Olympus Optical Co., Ltd., Tokyo, Japan

[21] Appl. No.: 974,501

[22] Filed: Dec. 29, 1978

[30] Foreign Application Priority Data

Jan. 9, 1978 [JP] Japan ................... 53-536

[51] Int. Cl.³ ............ A61B 1/00; G02B 3/00; G02B 5/17; G02B 9/34
[52] U.S. Cl. ................... 350/469; 128/4; 350/96.26; 350/415
[58] Field of Search ......... 350/175 TS, 96.26, 220; 128/4

[56] References Cited

U.S. PATENT DOCUMENTS

| | | | |
|---|---|---|---|
| 3,090,378 | 5/1963 | Sheldon et al. | 128/4 |
| 3,497,701 | 2/1970 | Dalton | 350/175 TS X |
| 3,576,358 | 4/1971 | Hayamizu et al. | 350/175 TS X |

*Primary Examiner*—John K. Corbin
*Assistant Examiner*—Scott J. Sugarman
*Attorney, Agent, or Firm*—Cushman, Darby & Cushman

[57] ABSTRACT

A method for focusing an objective lens of endoscope comprising dividing said objective lens into a front lens group and a rear lens group, arranging an optical fiber bundle so as to have its end surface on the rear side of said rear lens group and focusing said objective lens by displacing said rear lens group together with said optical fiber bundle. This method makes it possible to afford high magnification level for the objective lens even when it is brought into focus with an object located at a short distance.

2 Claims, 10 Drawing Figures

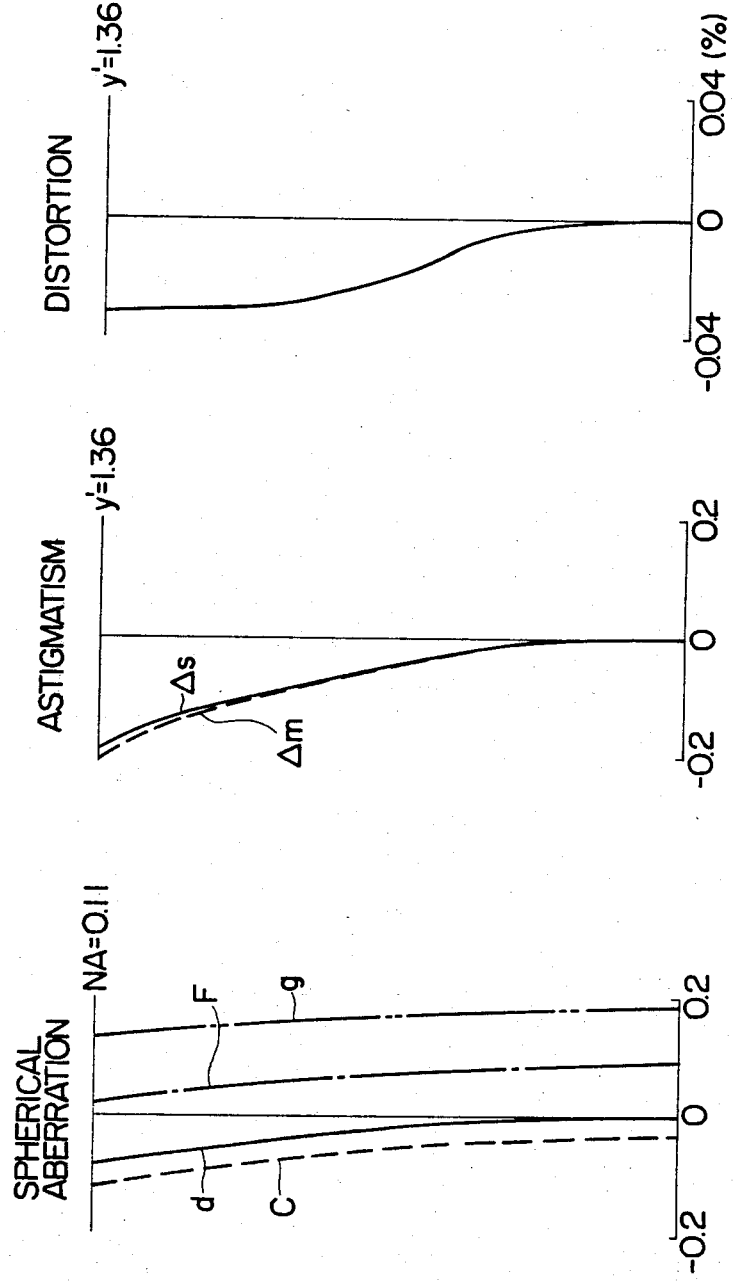

METHOD FOR FOCUSING AN OBJECTIVE LENS OF ENDOSCOPE

BACKGROUND OF THE INVENTION (a) Field of the Invention

The present invention relates to a method for focusing an objective lens of endoscope.

(b) Description of the Prior Art

It is required for an endoscope to be capable of observing areas as wide as possible in case of observing an object located at a long distance and also to observe a narrow area with said endoscope kept close to said area so as to comprehend abnormal portion minutely without overlooking. For observing an object located at a short distance, an endoscope should preferably have high magnification and must permit proper focusing at such high magnification level.

For focusing an objective lens of an endoscope, there has conventionally been known a method to displace an optical fiber bundle 1 as shown in FIG. 1A and FIG. 1B (for example, the method disclosed by Japanese Published Unexamined Utility Model Application No. 99087/74). Speaking more concretely, the optical fiber bundle 1 is retreated for a distance of $\Delta_0 = f_0 \beta_0$ (wherein the reference symbol $f_0$ represents focal length of an objective lens 2 and the reference symbol $\beta_0$ designates magnification level of the objective lens 2) for setting the endoscope at the position to observe an object located at a short distance shown in FIG. 1B from the position for observing an object located at a long distance shown in FIG. 1A. As is clear from the figures, this method had a drawback that the principal rays falls on the optical fiber bundle at a large angle of incidence and transmitted light intensity is lower at marginal portions of the optical fiber bundle, thereby darkening marginal portions on an image formed with the optical fiber bundle.

Further, there has conventionally been known another method for focusing an objective lens of an endoscope which comprises dividing an objective lens 2' into two groups 2'a and 2'b as illustrated in FIG. 2A and FIG. 2B, and changing the distance between said two lens groups (for example, the method disclosed by Japanese Published Examined Utility Model Application No. 2194/75). Speaking more concretely, the lens group 2'b arranged on the side of the optical fiber bundle 1 is displaced for setting the endoscope at the position for observing an object O located at a short distance shown in FIG. 2B from the position at which said objective lens is focused on an object located at a long distance shown in FIG. 2A. However, this method also had a drawback that it cannot provide sufficiently high magnification level since the objective lens has a short focal length when it is focused with the object O located at a short distance.

SUMMARY OF THE INVENTION

A general object of the present invention is to provide a method for focusing an objective lens of an endoscope which comprises dividing an objective lens into a front lens group and a rear lens group, arranging an optical fiber bundle so as to have its end surface on the rear side of said rear lens group and changing the distance between said front and rear lens groups to focus the objective lens with an object located at a short distance by displacing said rear lens group together with said optical fiber bundle.

BRIEF DESCRIPTION OF THE DRAWINGS

FIG. 6 shows graphs illustrating the aberration characteristics of said objective lens when it is focused on an object located at 3 mm.

DESCRIPTION OF THE PREFERRED EMBODIMENTS

Figure 1A:
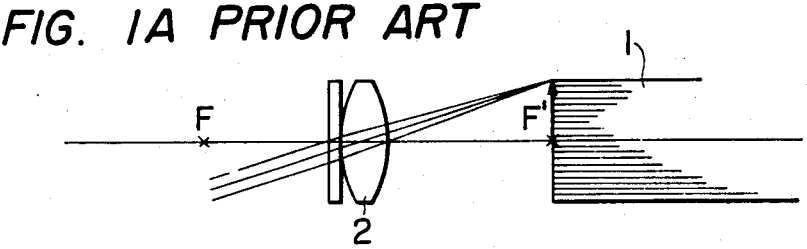
FIG. 1A, FIG. 1B, FIG. 2A and FIG. 2B show sectional views illustrating the conventional method for focusing the objective lens of an endoscope.
Figure 1B:
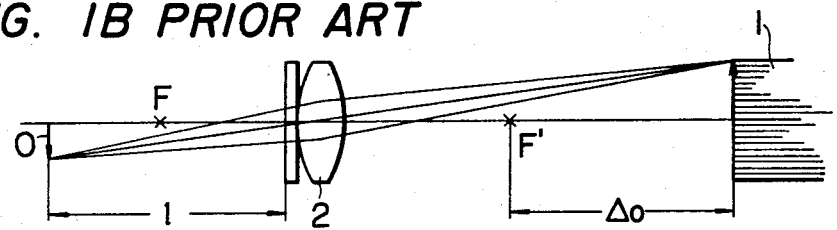
Figure 2A:
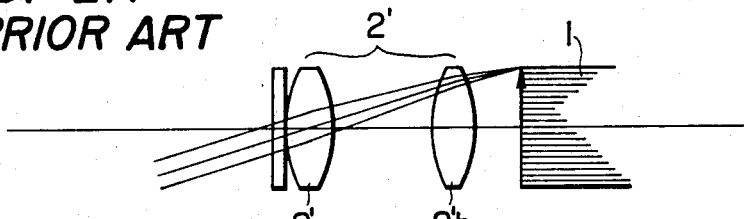
Figure 2B:
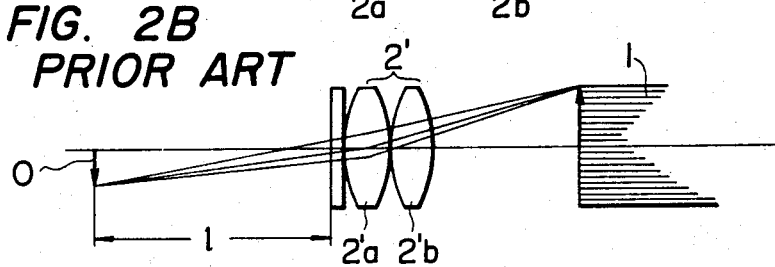
Figure 3A:
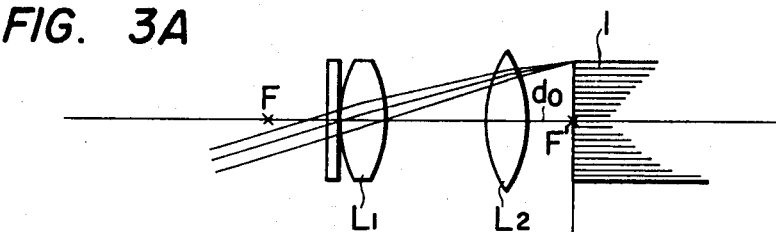
FIG. 3A and FIG. 3B show sectional views illustrating the method for focusing the objective lens of an endoscope according to the present invention.
Figure 3B:
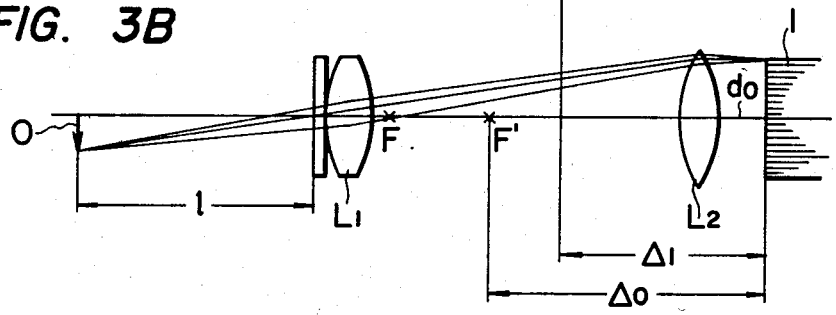

The focusing method according to the present invention comprises dividing an objective lens into a front lens group $L_1$ and a rear lens group $L_2$ as shown in FIG. 3A and FIG. 3B and displacing said rear lens group $L_2$ together with an optical fiber bundle 1 so as to change the distance between said front lens group $L_1$ and said rear lens group $L_2$, thereby bringing the objective lens in good focus. Further, the objective lens for endoscope adapted for the focusing method according to the present invention is so designed as to satisfy the following condition:

$$f < f_1 < \sqrt{2}\, f$$

FIG. 3A shows said objective lens in the condition in which it is focused on an object located at a long distance, whereas FIG. 3B illustrates it in the condition in which it is focused on an object located at a short distance. Speaking concretely, the objective lens is brought into focus with an object O located at a short distance by displacing the rear lens group $L_2$ of the objective lens together with the optical fiber bundle 1 from the position shown in FIG. 3A to that illustrated in FIG. 3B while keeping gap $d_0$ therebetween always constant. This focusing method enables the principal ray to be incident at a small angle on the optical fiber bundle. Further, it can afford high magnification for an object located as short distance.

When the objective lens is focused on an object located at infinite distance, its total focal length f can be expressed by the formula (1) shown below:

$$f = f_1 \cdot \beta_2 \tag{1}$$

wherein the reference symbol $f_1$ represents focal length of the front lens group $L_1$ and the reference symbol $\beta_2$ designates magnification level of the rear lens group $L_2$.

Magnification level $\beta$ of the objective lens when it is focused on an object located at infinite distance can be expressed by the formula (2) given below:

$$\beta = \beta_1 \cdot \beta_2 \tag{2}$$

wherein the reference symbol $\beta_1$ represents magnification level of the front lens group.

Further, displacement $\Delta_1$ can be expressed by formula (3) shown below:

$$\Delta_1 = f_1 \cdot \beta_1 \qquad (3)$$

Form the formulae mentioned above, displacement $\Delta_1$ can be expressed as follows:

$$\Delta_1 = f \cdot \beta \cdot (f_1/f)^2$$

Since the distance $\Delta_0$ as measured from the rear focal point of the objective lens to the end surface of said optical fiber bundle is equal to $f \cdot \beta$, $\Delta_1$ can be expressed as follows:

$$\Delta_1 = \Delta_0 (f_1/f)^2 \qquad (4)$$

Too long displacement of the optical fiber bundle is undesirable since it may easily break the fibers and will prolong the distal end of the endoscope. It is therefore required to limit $\Delta_1$ within a range of $\Delta_1 < 2\Delta_0$. Therefore, $(f_1/f)^2$ in the formula (4) should be:

$$(f_1/f)^2 < 2$$

Further, the rear focal point of the objective lens (image forming position when the objective lens is focused on an object located at infinite distance) must be located on the rear side of the final surface of the objective lens and, therefore $\beta_2$ must be smaller than 1. Since $\beta = (f/f_1) < 1$ from the formula (1), the objective lens must satisfy the following condition:

$$f_1 > f \qquad (6)$$

From the formulae (5) and (6) mentioned above, the focal length $f_1$ of the front lens group must be so selected as to satisfy the condition defined below:

$$f < f_1 < \sqrt{2} f$$

Now, numerical data for the objective lens for endoscope adapted for the focusing method according to the present invention will be shown below:

| | | | |
|---|---|---|---|
| $r_1 = 1.0630$ | | | |
| | $d_1 = 0.426$ | $n_1 = 1.6968$ | $\nu_1 = 55.5$ |
| $r_2 = -0.6843$ | | | |
| | $d_2 = 0.128$ | $n_2 = 1.78472$ | $\nu_2 = 25.7$ |
| $r_3 = 2.2051$ | | | |
| | $d_3 = 0.085$ | | |
| $r_4 = 1.9243$ | | | |
| | $d_4 = 0.128$ | $n_3 = 1.78472$ | $\nu_3 = 25.7$ |
| $r_5 = 0.4255$ | | | |
| | $d_5 = 0.426$ | $n_4 = 1.6968$ | $\nu_4 = 55.5$ |
| $r_6 = -0.8834$ | | | |
| | $d_6 = 0.340 \sim 1.888$ | | |
| $r_7 = \infty$ | | | |
| | $d_7 = 0.213$ | $n_5 = 1.51633$ | $\nu_5 = 64.2$ |
| $r_8 = -2.1277$ | | | |
| | $d_8 = 0.043$ | | |
| $r_9 = 2.1277$ | | | |
| | $d_9 = 0.213$ | $n_6 = 1.51633$ | $\nu_6 = 64.2$ |
| $r_{10} = \infty$ | | | |
| | $f = 1$ $F/3.0$ | $2\omega = 61°25'$ | |
| | $f_1 = 1.085$ | $TW = -10°47'$ | | wherein the reference symbols $r_1$ through $r_{10}$ represent radii of curvature on the surfaces of the respective lens elements, the reference symbols $d_1$ through $d_9$ designate thicknesses of the respective lens elements and airspaces therebetween, the reference symbols $n_1$ through $n_6$ denote refractive indices of the respective lens elements, the reference symbols $\nu_1$ through $\nu_6$ represent Abbe's numbers of the respective lens elements and the reference symbol TW designates the angle formed between the principal ray and the optical axis on the end surface of the optical fiber bundle.

Figure 4A:
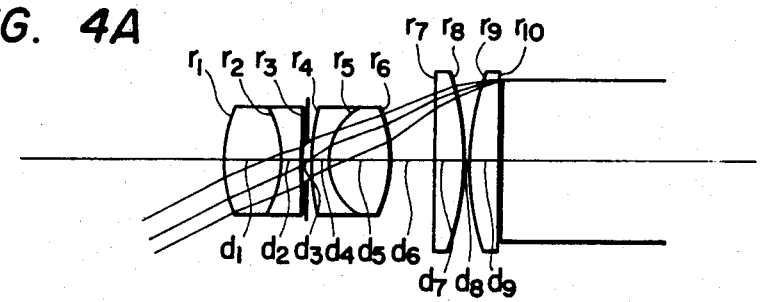
FIG. 4A and FIG. 4B illustrate sectional views clarifying an example of the objective lens for endoscope adapted for the focusing according to the present invention.
Figure 4B:
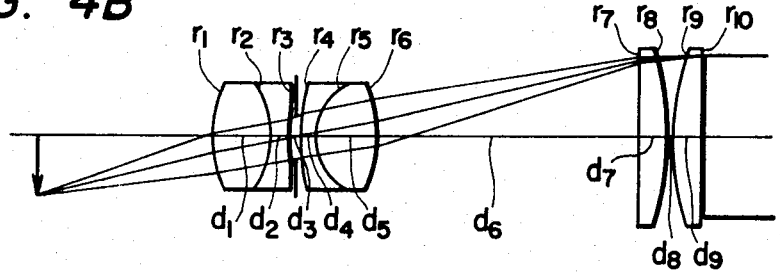
Figure 5:
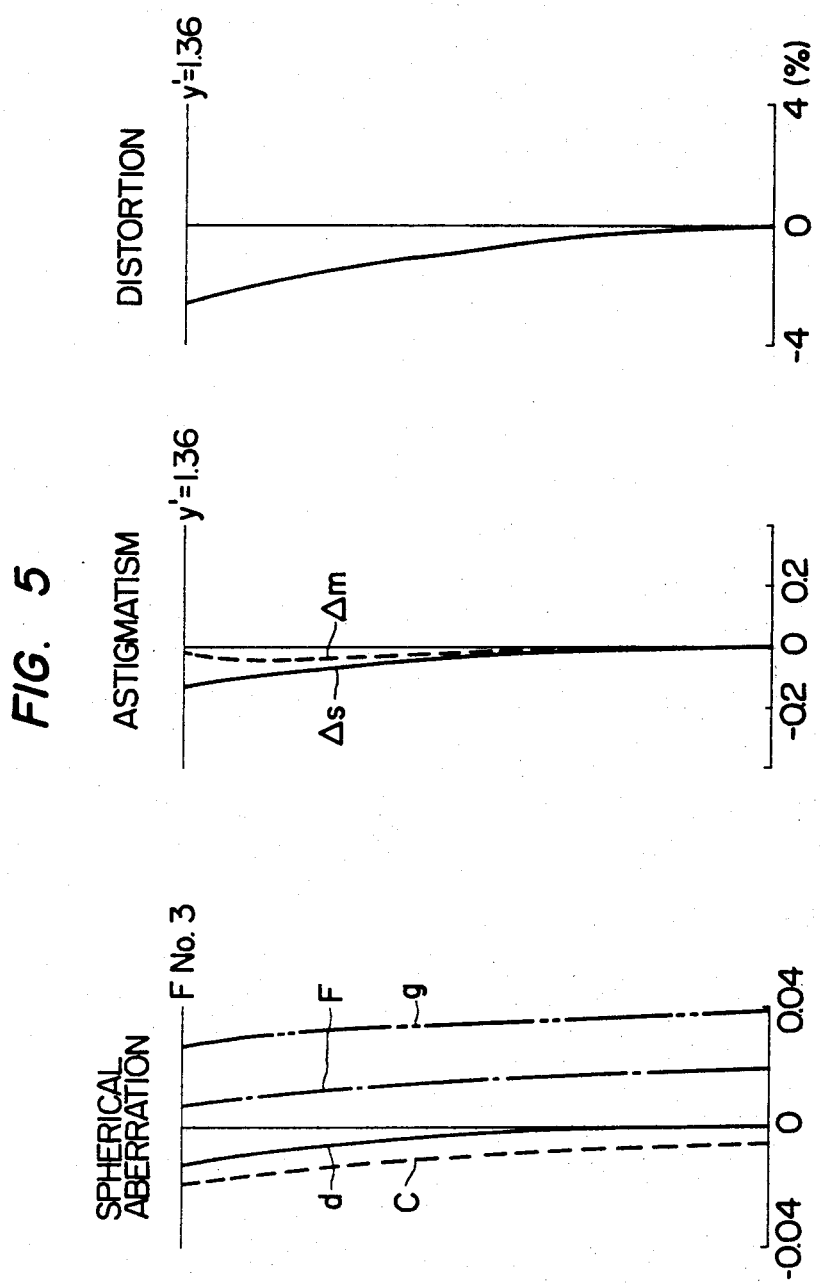
FIG. 5 shows graphs illustrating the aberration characteristics of said objective lens when it is focussed on an object located at infinite distance.

This example of the objective lens for endoscope has such a composition as illustrated in FIG. 4A and FIG. 4B, the former showing the objective lens when it is set at $d_6 = 0.340$ to be focused on an object located at infinite distance, whereas the latter illustrating said objective lens when it is set at $d_6 = 1.888$ to be focused on an object placed at a distance of 3 mm. In this example, the values of f, F, $2\omega$ and TW are given for $d_6 = 0.340$. When the objective lens is designed for $d_6 = 1.888$, the values will be as listed below: $f = 3.215$, $F/3.0$, $2\omega = 28°12'$, $TW = 3°43'$ and $\beta = 1.315X$.

We claim:

1. An objective optical system for endoscopes comprising an objective lens system consisting of a front lens group and a rear lens group, and an optical fiber bundle, said front lens group being fixed to the body of the endoscope, whereas said rear lens group and said optical fiber bundle being movable along the optical axis while keeping the relative interval therebetween at a constant distance, said objective optical system satisfying the following conditions:

$$f < f_1 < \sqrt{2} f$$

wherein the reference symbol $f_1$ represents focal length of said front lens group and the reference symbol f designates focal length of said objective lens system as a whole.

2. An objective optical system for endoscopes comprising an objective lens system consisting of a front lens group and a rear lens group, and an optical fiber bundle, said front lens group being fixed to the body of the endoscope, whereas said rear lens group and said optical fiber bundle being movable along the optical axis while keeping the relative interval therebetween at a constant distance, said objective optical system having the following numerical data:

| | | | |
|---|---|---|---|
| $r_1 = 1.0630$ | | | |
| | $d_1 = 0.426$ | $n_1 = 1.6968$ | $\nu_1 = 55.5$ |
| $r_2 = -0.6843$ | | | |
| | $d_2 = 0.128$ | $n_2 = 1.78472$ | $\nu_2 = 25.7$ |
| $r_3 = 2.2051$ | | | |
| | $d_3 = 0.085$ | | |
| $r_4 = 1.9243$ | | | |
| | $d_4 = 0.128$ | $n_3 = 1.78472$ | $\nu_3 = 25.7$ |
| $r_5 = 0.4255$ | | | |
| | $d_5 = 0.426$ | $n_4 = 1.6968$ | $\nu_4 = 55.5$ |
| $r_6 = 0.8834$ | | | |
| | $d_6 = 0.340 \sim 1.888$ | | |
| $r_7 = \infty$ | | | |
| | $d_7 = 0.213$ | $n_5 = 1.51633$ | $\nu_5 = 64.2$ |
| $r_8 = -2.1277$ | | | |
| | $d_8 = 0.043$ | | |
| $r_9 = 2.1277$ | | | |
| | $d_9 = 0.213$ | $n_6 = 1.51633$ | $\nu_6 = 64.2$ |
| $r_{10} = \infty$ | | | |
| | $f = $ $F/3.0$ | $2\omega = 61°25'$ | |
| | $f_1 = 1.085$ | $TW = -10°47'$ | | wherein the reference symbols $r_1$ through $r_{10}$ represent radii of curvature on the surfaces of the respective lens element, the reference symbols $d_1$ through $d_{10}$ designate thicknesses of the respective lens elements and airspaces therebetween, the reference symbols $n_1$ through $n_6$ denote refractive indices of the respective lens elements, the reference symbols $\nu_1$ through $\nu_6$ represents Abbe's numbers of the respective lens elements and the reference symbol TW represents angle formed between the principal ray and optical axis on the end surface of the optical fiber bundle.

* * * * *